(12) United States Patent
Eichenberg

(10) Patent No.: US 8,714,972 B2
(45) Date of Patent: May 6, 2014

(54) SELF-LIGATING BRACKET

(76) Inventor: Tena Eichenberg, Neu-Ulm (DE)

( * ) Notice: Subject to any disclaimer, the term of this patent is extended or adjusted under 35 U.S.C. 154(b) by 0 days.

(21) Appl. No.: 13/382,357

(22) PCT Filed: Jul. 19, 2010

(86) PCT No.: PCT/EP2010/060427
§ 371 (c)(1),
(2), (4) Date: Jan. 5, 2012

(87) PCT Pub. No.: WO2011/012486
PCT Pub. Date: Feb. 3, 2011

(65) Prior Publication Data
US 2012/0107760 A1 May 3, 2012

(30) Foreign Application Priority Data

Jul. 31, 2009 (CH) ........................................ 1203/09

(51) Int. Cl.
*A61C 3/00* (2006.01)
(52) U.S. Cl.
USPC ............................................. 433/10; 433/20
(58) Field of Classification Search
USPC ............................................. 433/10–15, 20
See application file for complete search history.

(56) References Cited

U.S. PATENT DOCUMENTS

| 3,052,028 | A | * | 9/1962 | Wallshein | 433/11 |
| 5,174,753 | A | | 12/1992 | Wool | |
| 6,663,385 | B2 | | 12/2003 | Tepper | |
| 7,033,170 | B2 | * | 4/2006 | Cordato | 433/10 |
| 2003/0118967 | A1 | * | 6/2003 | Tepper | 433/11 |
| 2006/0105286 | A1 | * | 5/2006 | Raby et al. | 433/24 |
| 2007/0148610 | A1 | * | 6/2007 | Lai et al. | 433/11 |

FOREIGN PATENT DOCUMENTS

EP 1754450 A1 2/2007

* cited by examiner

Primary Examiner — Eric Rosen
(74) Attorney, Agent, or Firm — Hoffmann & Baron, LLP

(57) ABSTRACT

Disclosed is a bracket including a base plate on which two retaining wings are formed running parallel to one another and defining an intermediate space in which a wire arch may be held. The intermediate space has a trapezoidal structure such that the wire arch is always pushed upward under the elasticity of the bracket by the inclined retaining wings toward the retaining surfaces, such that the wire arch is held in the intermediate space in an aligned fashion without play. The cross sectional shape of the wire arch is selected such that no surface contact occurs in the intermediate space.

14 Claims, 5 Drawing Sheets

SELF-LIGATING BRACKET

The present invention relates to a self-ligating bracket and a wire arch consisting of a nickel-titanium alloy to be accommodated therein, with a retaining plate and at least a pair of spaced apart retaining wings integrally joined thereto, between which the wire arch is snapped in place, wherein the at least one retaining wing pair defines a gap that extends in the longitudinal direction of the wire arch, wherein the cross section of the gap exhibits a trapezoidal shape, and the retaining wings exhibit tongues at the ends remote from the retaining plate.

Brackets for regulating the position of teeth were originally made out of relatively rigid material, and the wire arch incorporated in the bracket was secured with ligatures. Developed later were the self-ligating brackets, in which the wire arch (archwire) was fixed in the bracket by means of a spring or clip (clip), so as to thereby largely avoid the time-consuming ligatures.

In the last several years, mention has also been made of self-ligating brackets consisting of elastic materials, which make it possible to press a wire arch between one or more pairs of retaining wings and snap it in place, so that the wire arch is held in the bracket.

Both plastics and shape memory alloys (e.g., comprised of nickel titanium) have been proposed as the used elastic materials. Precisely the latter material has become widespread in orthodontic technology, since the archwire is very often fabricated out of a nickel titanium alloy with a super-elastic behavior or memory effect.

Among other factors, the precision, and hence success, of orthodontic treatment depends on how the orthodontic arch is guided in the slot of the bracket. The objective here is to achieve the least clearance possible, even though too tight a fit will lead to elevated friction between the slot and arch, and hence slow the movement of the teeth.

Already known from document U.S. Pat. No. 5,356,289 A is an orthodontic bracket, which is made out of a nickel titanium alloy with memory effect or plastic, wherein two retaining wing pairs are present, between which an archwire with a rectangular cross section can be snapped in place. The cross section of the gap between the retaining wings is essentially rectangular as well.

The gap between the two retaining wings must inevitably be larger than the cross section of the archwire. As a consequence, the wire arch lies between the retaining wings with a clearance, resulting in a diminished precision of tooth movement, and hence a poorer treatment result. If the wire arch were to exactly match the shape of the gap between the retaining wings, the wire arch would be held free of clearance, but this cannot be accomplished in reality without simultaneously impeding the contouring of the wire arch.

The solution according to document U.S. Pat. No. 6,663,385 B is associated with precisely the same conceptual error. While the solution shown here essentially corresponds to the embodiment discussed above, the two retaining wings in this case are configured to extend over the entire length of the retaining plates. In order to increase the flexibility of the retaining wings, longitudinal grooves are provided on the wings in the area of the retaining plate, and intended to act as hinges. However, the problem remains the same. The wire arch in no way runs exactly straight, making it impossible to achieve a tight fit, as depicted here both in relation to the wire arch with a rectangular cross section and in the case of round wire arches. But in the final analysis, this document also shows a variant on FIG. 19 in which the gap between the two retaining wings has a trapezoidal design. The base surface of the trapezoid here runs flush with the surface of the retaining plate. As depicted on FIG. 19, this embodiment otherwise reflects the most obvious prior art of the present invention as defined at the outset, wherein the conicity of the thickness of the retaining wings is here intended to replace the longitudinal wings mentioned above, which produce the hinge-like effect. Accordingly, the same archwire with a rectangular cross section is used. Something other than the desired form-fit seating is also not disclosed here.

WO 2006/014378 shows another slightly modified version of a self-ligating bracket. In this solution, a round archwire is used, and the tongues are outwardly lengthened so that the archwire can be removed. However, we do not believe this is necessary, since the archwire is usually not reused, and thus can be extracted more easily by sectioning it in its longitudinal direction.

The object of the present invention is to realize a bracket and a wire arch with a correspondingly adjusted shape, which aligns itself after snapped in, causing it to be seated free of clearance.

This object is achieved by a bracket and a wire arch according to the preamble of claim 1, which exhibit the characterizing features of claim 1.

The drawing illustrates a preferred exemplary embodiment of the subject matter according to the invention, which is described based on the following specification with reference to the attached drawing. Shown on:

Figure 1:
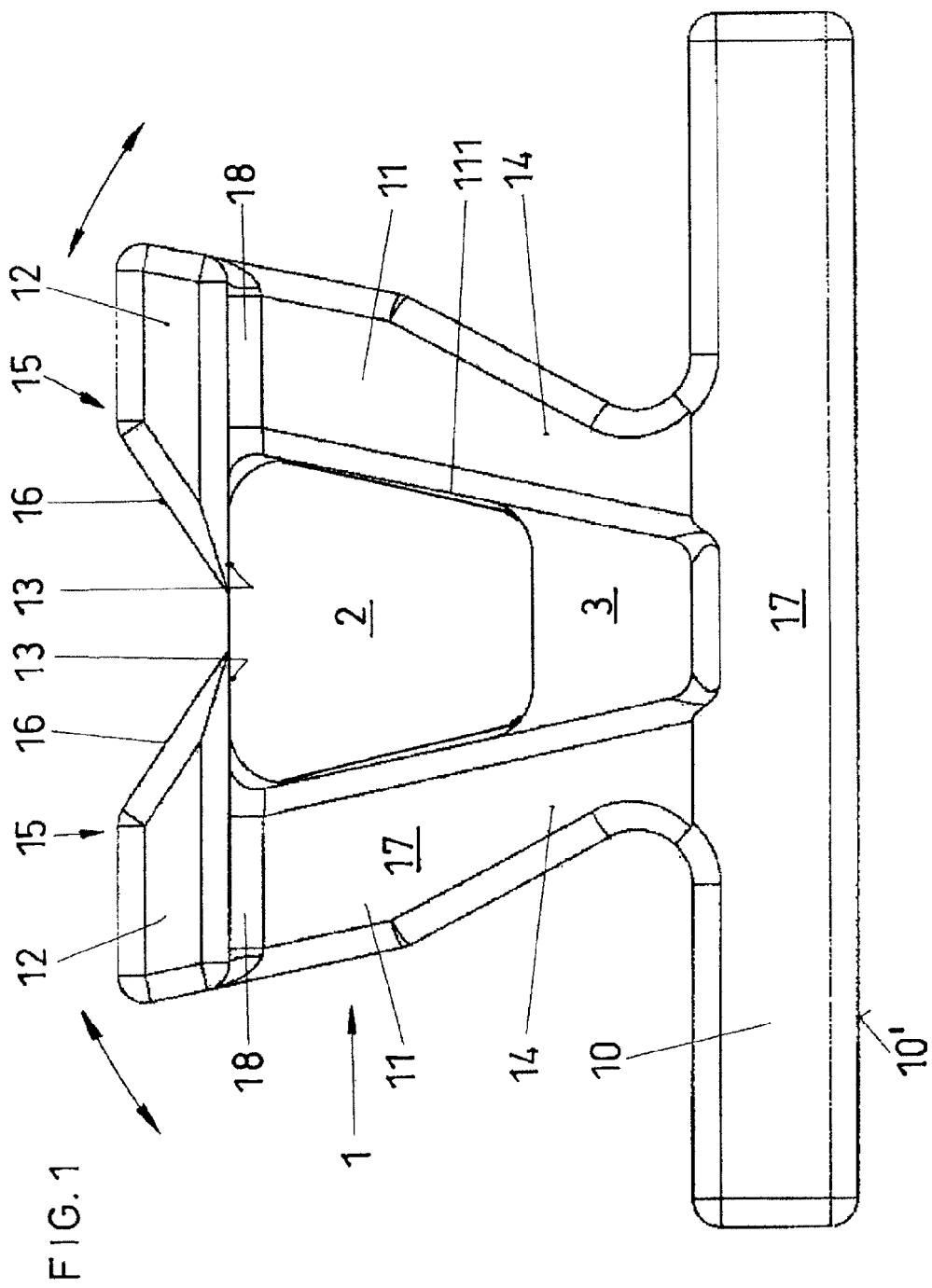
FIG. 1 is a side view of the bracket according to the invention with the accompanying wire arch inserted in the bracket.
Figure 2:
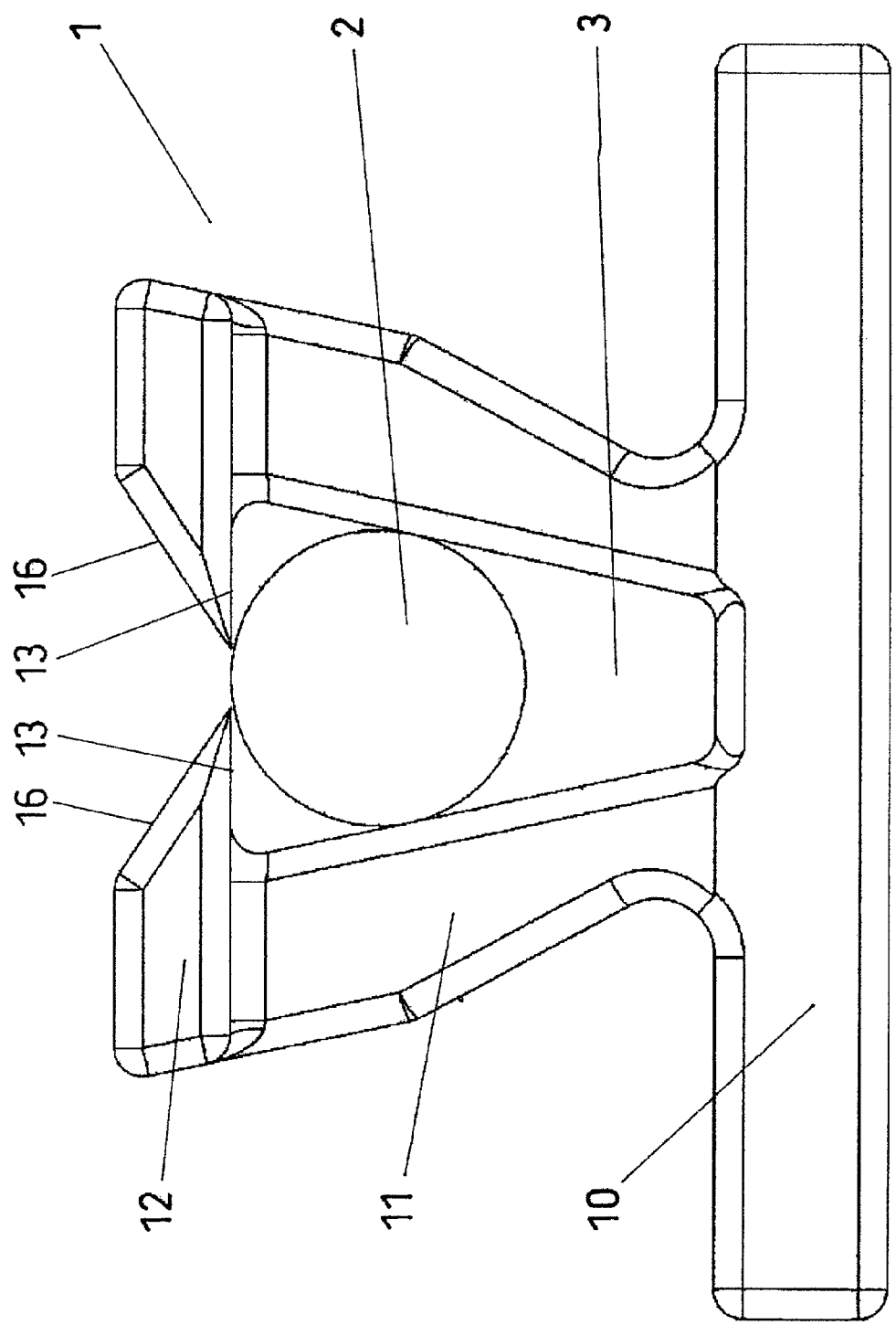
FIG. 2 is the same view of the same bracket with a conventional archwire having a round cross section.

A front view of a preferred embodiment of the bracket 1 according to the invention is shown on FIG. 1. 10 denotes the retaining plate, which exhibits an adhesive surface to be affixed to a tooth. The same bracket can here be situated both buccally and lingually. The adhesive surface of the retaining plate 10 is marked 10'. Visible in this view is the short side of the retaining plate 10, while the long side runs perpendicular to the drawing plane. Two retaining wings 11 spaced apart from each other are molded onto the surface of the retaining plate 10, essentially running mirror symmetrically relative to the longitudinal central axis. Viewed from the central longitudinal axis, the retaining wings 11 are essentially slightly curved toward the outside, and end in tongues 12. The bottom side of these tongues 12 terminally molded onto the retaining wings 11 exhibits retaining surfaces 13, which essentially run parallel to the surface of the retaining plate 10. The retaining wings 11 have a first, increasing section 14, in which the thickness of the wings increases in cross section, from the area near the retaining plate 10 toward the tongues 12. The area adjacent to this section and leading up to the tongues 12 forms a second section having a constant cross sectional area.

In addition to the already mentioned retaining surfaces 13 directed toward the retaining plate 10, the tongues 12 have upper sides 15. These sides 15 exhibit insertion ramps 16 that run from the upper side toward the retaining surfaces. These insertion ramps 16 make is possible to use a wire arch 2 that is round or a wire arch having a trapezoidal cross section, the narrow top surface 12 of which lies in this area of the insertion ramps, to outwardly deform the retaining wings 11 in a resilient manner simply by pressing on the wire arch 2, thereby snapping it in place in the gap 3 between the two retaining wings 11. The retaining wings 11 have inner lateral walls 111, which practically act as sliding ramps, and are able to slide the wire arch 2 into a defined upper position during the elastic restoration of the retaining wings 11. Certain conditions must be satisfied in relation to the wire arch 2 for the wire arch to now align itself and become seated in the gap 3 of the bracket 1 free of clearance. The wire arch 2 must be configured in such a way that, in the self-aligning, clearance-free position in the bracket 1, it comes to adjoin a respective abutment line of an inner lateral wall 111 of each retaining wing 11, in the process of which a resultant force directed toward the tongues 12 remains in place, holding the wire arch 2 in the defined position. In each case, the wire arch 2 is here spaced apart from the retaining plate 10 in the self-aligning, clearance-free retained position. As a consequence, the wire arch 2 is only aligned on the retaining wings 11, and non-positively abuts the tongues 12. Wire arches with varying cross sectional shapes can satisfy this condition. It is crucial that the cross sectional shape of the wire arch deviate from the cross sectional shape of the gap 3, and that the retaining wings 11 of the bracket 1 always be under a certain tension in the inserted state. Wire arches with preferred cross sectional shapes are those wire arches that exhibit either a round cross section or a trapezoidal cross section, wherein the isosceles, trapezoidal cross section exhibits a base surface slightly larger than the greatest distance between the two inner surfaces 111 of the retaining wings 11 with the latter slackened. The preferred diameter of a round wire arch 2 is roughly as large as a maximum inscribable circle in the gap 3 of the bracket 1. Of course, in order to again achieve the desired tension, this diameter must here be several percentage points greater to sustain a residual tension of the retaining wings 11. In this case, the wire arch will also bilaterally abut the pointed edges of the retaining tongues 12. The figure illustrates this situation in a clearly discernible manner.

Even in self-ligating brackets, ligatures or bands must often also be added to integrate all required tooth movements.

Therefore, it makes sense to provide an indentation 18 that runs approximately parallel to the retaining surfaces 13 in the bilateral faces 17 present on the bracket 1 arranged perpendicular to the running direction of the gap 3 in the transitional area between the retaining wings 11 and the terminal tongues 12. As a consequence, these indentations 18 run flush with the retaining surfaces 13. The dimensions of these indentations 18 must be adjusted to the used ligatures or rubber bands.

Figure 4:
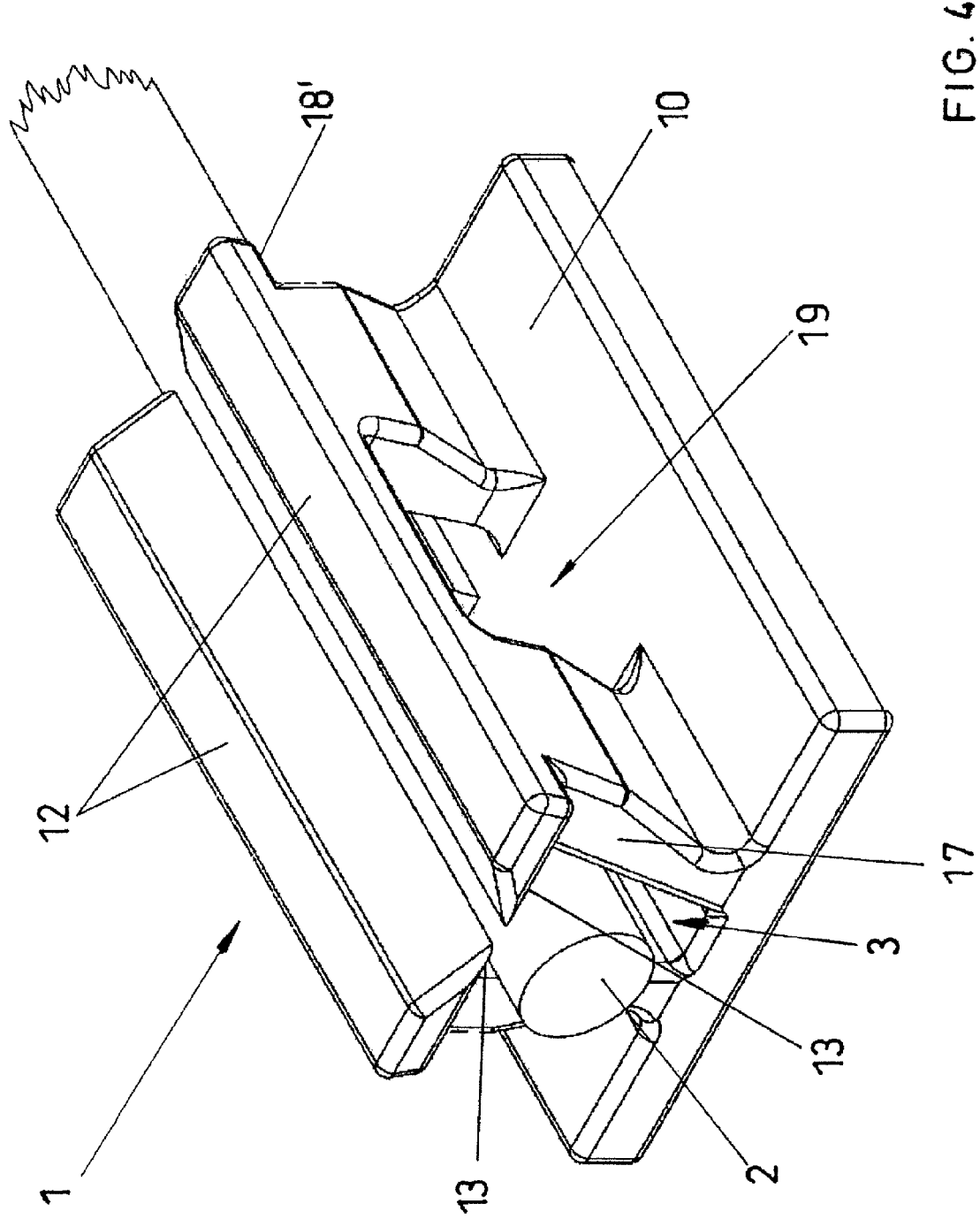
FIG. 4 shows a perspective view of the bracket according to the present invention with the round guidewire inserted.
Figure 5:
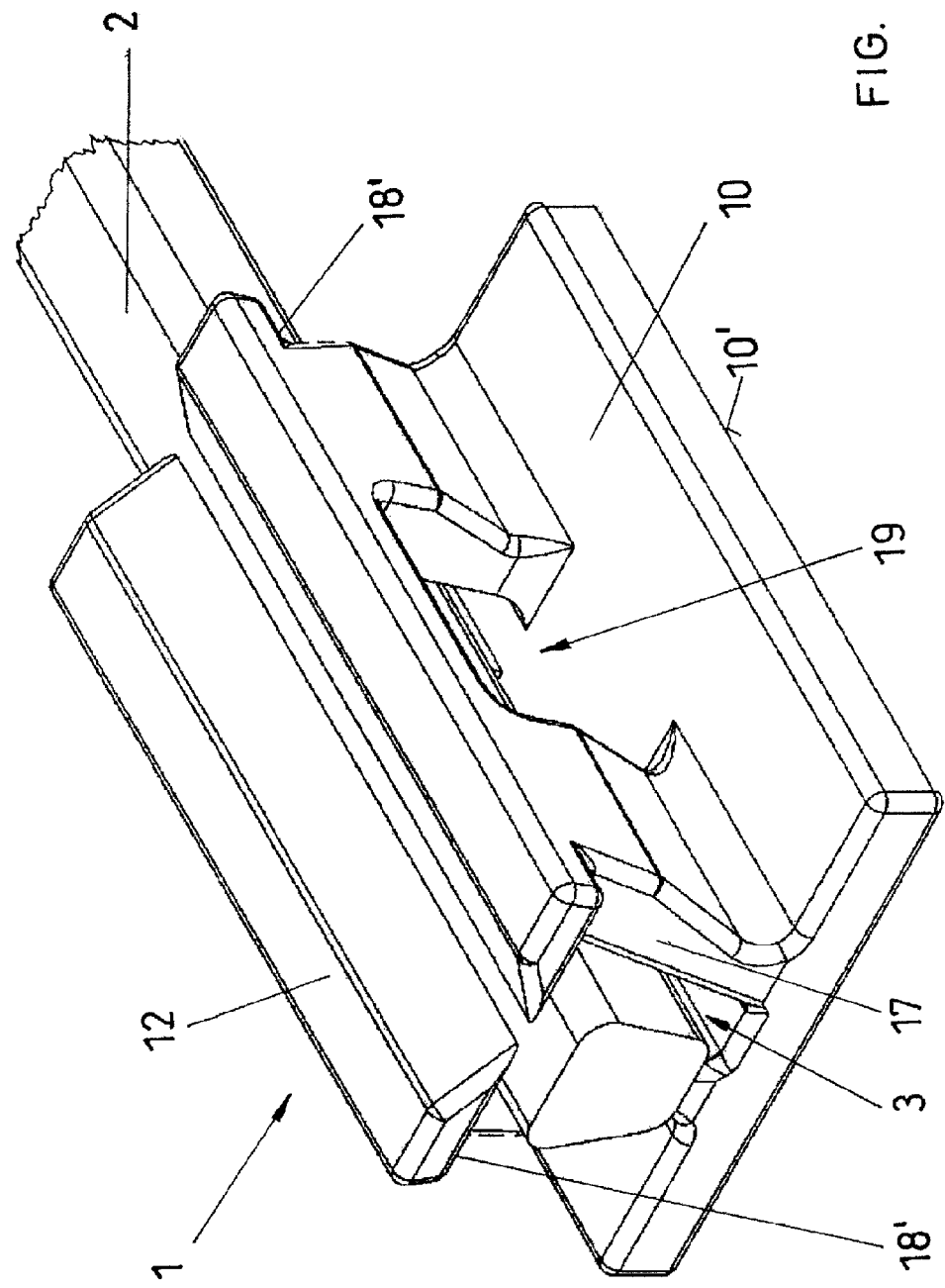
FIG. 5 shows the same view with trapezoidal wire arch inserted.

As evident from the perspective views on FIG. 4 and FIG. 5, the indentations 18 can be achieved by having the faces 17 of the two retaining wings 11 be slightly inclined from the retaining plate 10 to the tongues 12, so that the tongues project slightly on the front side relative to the retaining wings 11. This projection 18' now corresponds to the indentation 18.

The bracket 1 according to the invention provides both solutions involving several retaining wings arranged one after the other in the running direction of the wire arch, as well as variants with only one pair of retaining wings extending over the entire retaining plate length.

If only two retaining wings 11 extending over the entire length of the retaining plate 10 are present, it would make sense to introduce window-like openings 19 in the retaining wings 11, as clearly evident from the figures. In addition to the shapes of the openings or indentations depicted here, the bracket 1 according to the invention can of course exhibit differently configured indentations useful for incorporating a ligature.

Figure 3:
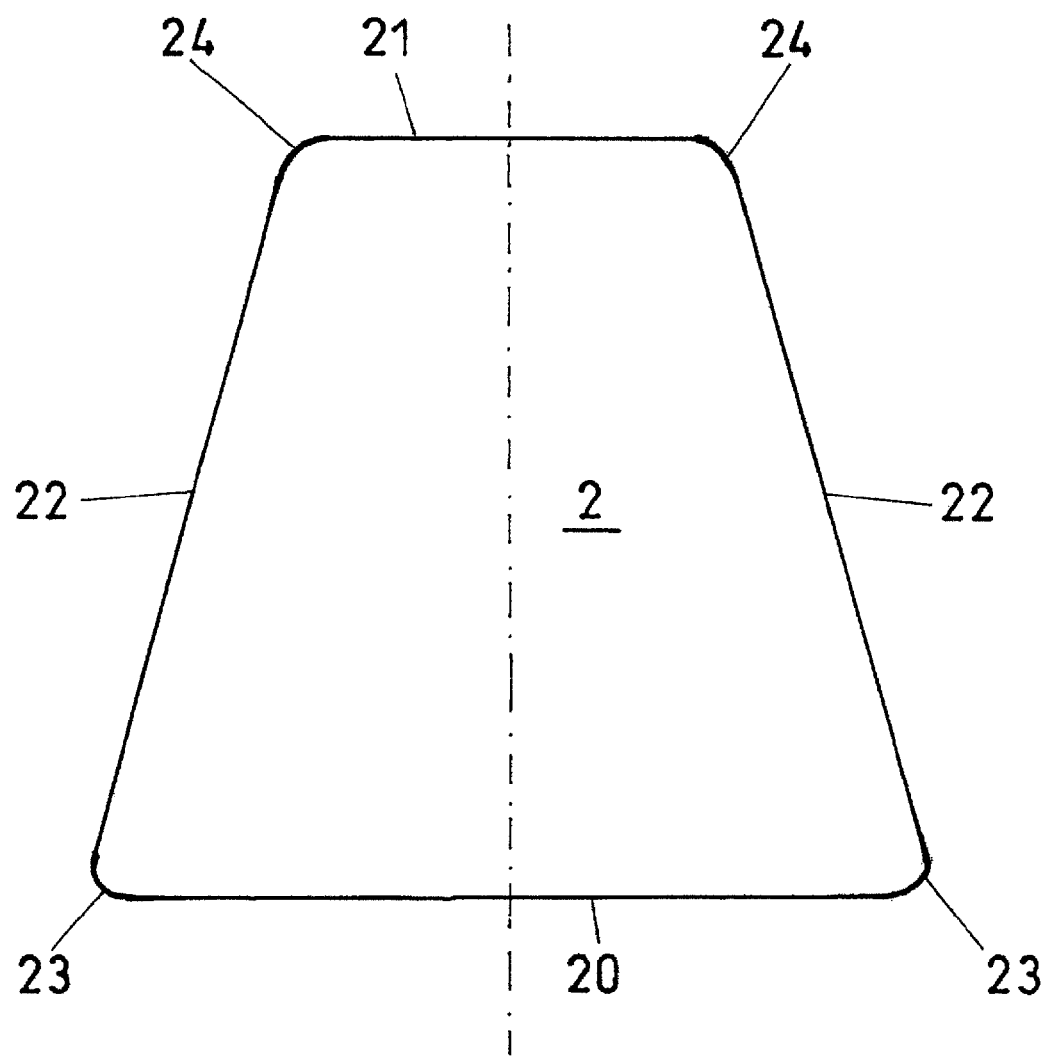
FIG. 3 shows a cross section through a preferred wire arch for use with brackets according to the invention.

FIG. 3 shows a cross section through a preferred embodiment of a wire arch. As already mentioned above, even though wire arches with various cross sectional shapes are possible, provided they satisfy the aforesaid conditions, a wire arch with a cross sectional shape in the configuration of an isosceles trapezoid is especially preferred. In this variant shown on FIG. 3, the wire arch exhibits a top surface 21 and a wider lower base surface 20 running parallel thereto. As a consequence, the lateral surfaces 22 run mirror symmetrically to the central, vertical longitudinal plane. The angle between the lateral surfaces 22 and base surface 20 is hence bilaterally acute, while the corresponding upper angle between the top surface 21 and lateral surface 22 is obtuse. Respective longitudinal edges 23 run between the base surface 20 and lateral surface 22. The upper longitudinal edges 24 run between the top surface 21 and lateral surfaces 22. These longitudinal edges 23 and 24 preferably exhibit a rounded configuration to optimize the way in which these self-centering edges slide along the inner lateral walls 111 of the retaining wings 11. However, the precondition for a self-centering, clearance-free seating is that the acute angle at the edge 23 between the base surface 20 and the lateral walls 22 be smaller than the angle included by the retaining surface 13 and the inner lateral wall 111 of the retaining wings 11. The angle included by the two lateral surfaces 111 in their extension with each other must necessarily be greater than the angle that the inner lateral walls 111 of the retaining wings 11 would include between each other, also in the extension with each other.

Because nickel titanium alloys with a memory effect are used, an elastic restoration first takes place when pressing in the wire arch, or archwire, which forces the wire arch into the desired clearance-free, abutting position as described before, wherein the archwire is pressed against the retaining surfaces, while the lateral surfaces are only guided. After a certain time and exposed to the warmth n of the oral cavity, a plastic restoration then takes place, and hence a relatively tight abutment of the retaining wings on the lateral surfaces 22 of the archwire, thereby producing a relatively tight abutment, and thus increasing the friction between the slot formed by the retaining wings 11 and the retaining surfaces 13 and the wire arch 2. This causes the teeth to move more slowly. However, this is preferred in dental orthopedics, since a return movement that also always happens after treatment is significantly reduced. The same effect is also encountered in wire arches with a round cross section, since the surfaces 111 of the retaining wings 11 here cling slightly flatly to the wire to a slight extent as well.

When working with a wire arch (2) (archwire) having a round cross section, the latter must also be adjusted to the gap (3) of the bracket (1) when selecting the size. In principle, the diameter of the wire arch must be large enough that the retaining wings (11) under a pretension move the wire arch (2) up, until it comes to abut the bottom side of the tongues (12). This is generally satisfied when the diameter of the wire arch is greater than the diameter of the maximum circle inscribable in the gap (3). Of course, there is a limit to how much larger the diameter of the wire arch can be relative to the aforementioned inscribable circle. However, experience will guide the expert in properly dimensioning the latter. In principle, it is enough that the diameter be only a few percentage points larger than the maximum circle inscribable in the gap, in particular between 2 and 20%.

As already mentioned, cross sectional shapes other than the two embodiments of the archwire or wire arch shown here are also conceivable. For example, the lateral surfaces 22 of the wire arch 2 can bulge outward slightly. An archwire with a triangular shape is also conceivable. In this case, the cross section of the gap 3 is also such that the trapezoidal form also exhibits a very short top surface (base surface on the retaining plate 10 between the retaining wings 11).

REFERENCE LIST

1 Bracket
2 Wire arch (archwire)
3 Gap
10 Retaining plate
10' Adhesive surface
11 Retaining wing
12 Tongues
13 Retaining surfaces
14 Increasing section of retaining wings
15 Side remote from retaining plate
16 Insertion ramps
17 Face of bracket
18 Indentation
18' Projection
19 Window-like opening
20 Base surface
21 Top surface
22 Lateral surfaces
23 Longitudinal edges of base surface
24 Longitudinal edges of top surface
111 Inner lateral wall of retaining wing 11

The invention claimed is:

1. An assembly comprising a self-ligating bracket and a wire arch to be accommodated in the bracket, the bracket comprising a retaining plate securable to a tooth and a pair of spaced apart retaining wings integrally joined to the retaining plate, between which the wire arch is snapped in place, wherein the pair of spaced apart retaining wings defines a gap that extends in a longitudinal direction of the wire arch, wherein a cross section of the gap has a trapezoidal shape, and the pair of spaced apart retaining wings comprises a pair of tongues that extend toward each other at ends remote from the retaining plate, wherein the pair of tongues comprises retaining surfaces running at least approximately parallel to a surface of the retaining plate on a side facing toward the gap, wherein a cross section of the wire arch has a trapezoidal shape that includes a base surface and a narrower top surface, a width of the base surface being greater than a maximum distance between the pair of spaced apart retaining wings in a non-tensioned state, wherein the pair of spaced apart retaining wings is inclined from the retaining plate and away from each other to slide the wire arch away from the retaining plate toward the retaining surfaces of the pair of tongues to provide a self-aligning, clearance-free seating of the wire arch tensioned in the gap by the pair of spaced apart retaining wings and abutting the retaining surfaces of the pair of tongues.

2. The assembly according to claim 1, wherein the trapezoidal shape of the wire arch is an isosceles trapezoid.

3. The assembly according to claim 1, wherein a height of the wire arch is at least 10% smaller than a distance between the retaining plate and the retaining surfaces of the tongues.

4. The assembly according to claim 1, wherein each retaining wing of the pair of spaced apart retaining wings increases in thickness along at least one section from the retaining plate toward the pair of tongues.

5. The assembly according to claim 1, wherein the pair of tongues, on a side remote from the retaining plate, runs at an inclination toward a free end of the pair of tongues to form insertion ramps.

6. The assembly according to claim 1, wherein an indentation running approximately parallel to the retaining surfaces of the pair of tongues is present in bilateral faces of the bracket arranged perpendicular to a running direction of the gap in a transitional area between the pair of spaced apart retaining wings and the pair of tongues.

7. The assembly according to claim 1, wherein the pair of spaced apart retaining wings extends over an entire length of the retaining plate.

8. The assembly according to claim 7, wherein an opening is present in the pair of spaced apart retaining wings in an area between the pair of tongues and the retaining plate.

9. The assembly according to claim 1, wherein faces of the pair of spaced apart retaining wings are inclined from the retaining plate toward the pair of tongues such that the pair of tongues comprise projections relative to the faces.

10. An assembly comprising:
a wire arch having a cross section of a trapezoidal shape that includes a base surface and a narrower top surface, the base surface having a width; and
a self-ligating bracket, the bracket comprising:
a plate having a first surface and a second surface, the first surface securable to a tooth;
a pair of wings extending at an incline from the second surface and away from each other to define a gap between the pair of wings and the second surface, the width of the base surface of the wire arch being greater than a maximum distance between the pair of wings in a non-tensioned state, the pair of wings to receive the wire arch in the gap in a first tensioned position in which the wire arch is forced away from the second surface toward terminal ends of the pair of wings; and
a pair of tongues extending from the terminal ends of the pair of wings toward each other to partially enclose the gap, the pair of tongues to abut the wire arch as the wire arch is forced toward the terminal ends by the pair of wings to secure the wire arch in the gap in a second tensioned position.

11. The assembly according to claim 10, wherein the wings of the pair of wings increase in thickness along at least one section from the second surface of the plate toward the pair of tongues.

12. The assembly according to claim 10, wherein the tongues of the pair of tongues include insertion ramps to allow the pair of wings to deflect resiliently from one another to receive the wire arch into the gap.

13. The assembly according to claim 10, wherein the tongues of the pair of tongues include surfaces facing the gap that are approximately parallel to the second surface.

14. The assembly according to claim 10, wherein a cross-section of the gap has a substantially trapezoidal shape and the cross-section of the wire arch deviates from the cross-section of the gap.

\* \* \* \* \*